US010750967B2

(12) United States Patent
Bars et al.

(10) Patent No.: US 10,750,967 B2
(45) Date of Patent: Aug. 25, 2020

(54) REGIONAL HIGH-DENSITY MAPPING OF THE ATRIAL FIBRILLATION SUBSTRATE (71) Applicant: SUBSTRATE HD, Marseilles (FR)

(72) Inventors: Clement Bars, Boulogne Billancourt (FR); Julien Seitz, Marseilles (FR)

(73) Assignee: SUBSTRATE HD, Marseilles (FR)

(*) Notice: Subject to any disclaimer, the term of this patent is extended or adjusted under 35 U.S.C. 154(b) by 328 days.

(21) Appl. No.: 15/539,191

(22) PCT Filed: Dec. 23, 2015

(86) PCT No.: PCT/EP2015/081193
§ 371 (c)(1),
(2) Date: Jun. 23, 2017

(87) PCT Pub. No.: WO2016/102685
PCT Pub. Date: Jun. 30, 2016

(65) Prior Publication Data
US 2017/0367601 A1 Dec. 28, 2017

(30) Foreign Application Priority Data
Dec. 23, 2014 (FR) ..................... 14 63232

(51) Int. Cl.
A61B 5/04 (2006.01)
A61B 5/00 (2006.01)
A61B 5/046 (2006.01)
(52) U.S. Cl.
CPC .......... A61B 5/04012 (2013.01); A61B 5/046 (2013.01); A61B 5/7264 (2013.01); A61B 5/7282 (2013.01)

(58) Field of Classification Search
CPC ............................ A61B 5/04012; A61B 5/046
See application file for complete search history.

(56) References Cited

U.S. PATENT DOCUMENTS

| 8,340,766 | B2 * | 12/2012 | Ryu ................... A61B 5/046 607/14 |
| 8,433,398 | B2 | 4/2013 | Zhang |
| 9,538,929 | B2 * | 1/2017 | Yang .............. A61B 5/04012 |
| 10,010,258 | B2 * | 7/2018 | Bunch .................. A61B 5/046 |
| 2010/0094274 | A1 * | 4/2010 | Narayan ............... A61B 5/046 606/33 |

(Continued)

FOREIGN PATENT DOCUMENTS

WO    WO 2005/115232 A1    12/2005

OTHER PUBLICATIONS

International Search Report for PCT/EP2015/081193 dated Mar. 8, 2016, 3 pages.

(Continued)

Primary Examiner — Eric D. Bertram
(74) Attorney, Agent, or Firm — Dority & Manning, P.A.

(57) ABSTRACT

The present invention concerns a method for identifying areas of the heart of a patient able to be involved in the perpetuation of atrial fibrillation. This method takes into account the reference cycle of the arrhythmia and has two variants: a local variant in which the areas of the heart are each analysed separately and a regional variant in which several areas of the heart are analysed together. The invention also concerns device for implementing said method a program and the medium thereof.

18 Claims, 5 Drawing Sheets (56) References Cited

U.S. PATENT DOCUMENTS

2012/0078129 A1* 3/2012 Bailin .................. A61B 5/042
600/508
2015/0057507 A1* 2/2015 Koyrakh ............... A61B 5/066
600/301

OTHER PUBLICATIONS

Boahene, et al. "Termination of Acute Atrial Fibrillation in the Wolff-Parkinson-White Syndrome by Procainamide and Propafenone: Importance of Atrial Fibrillatory Cycle Length", Journal of the American College of Cardiology, Elsevier, New York, NY, vol. 16, No. 6, Nov. 1, 1990, 7 pages.
Nademanee, et al. "A New Approach for Catheter Ablation of Atrial Fibrillation: Mapping of the Electrophysiologic Substrate", Journal of the American College of Cardiology, Elsevier, New York, NY, vol. 43, No. 11, Jun. 2, 2004, 10 pages.
Scherr, et al. "Automated Detection and Characterization of Complex Fractionated Atrial Electrograms in Human Left Atrium During Atrial Fibrillation", Heart Rhythm, Elsevier, US, vol. 4, No. 8, Aug. 2, 2007, 8 pages.
Seitz et al, "Automated Detection of Complex Franctionated Atrial Electrograms in Substrate-Based Atrial Fibrillation Ablation: Better Discrimination with a New Setting of Carto® Algorithm", Journal for Atrial Fibrillation: JAFIB, vol. 6, No. 2, Jan. 2013, 8 pages.

* cited by examiner

CFAE

REGIONAL HIGH-DENSITY MAPPING OF THE ATRIAL FIBRILLATION SUBSTRATE

CROSS REFERENCE TO RELATED APPLICATION

This application is the national stage entry of International Patent Application No. PCT/EP2015/081193 having a filing date of Dec. 23, 2015, which claims priority to and the benefit of French Patent Application No. 1463232 filed in the French Intellectual Property Office on Dec. 23, 2014, the entire contents of which are incorporated herein by reference.

TECHNICAL FIELD

The present invention relates to the technical field of the identification of areas of the heart likely to be involved in a cardiac arrhythmia. More particularly, the present invention relates to a method and an apparatus for identifying areas of the heart likely to be involved in the initiation and the perpetuation of atrial fibrillation (AF).

STATE OF THE ART

Atrial fibrillation (AF), or sometimes commonly called "arrhythmia", is the most common and most complex heart rate disorder.

This heart rate disorder is manifested by a very rapid and disorganized atrial activity reflected by a fast and irregular heart rate.

Figure 1:
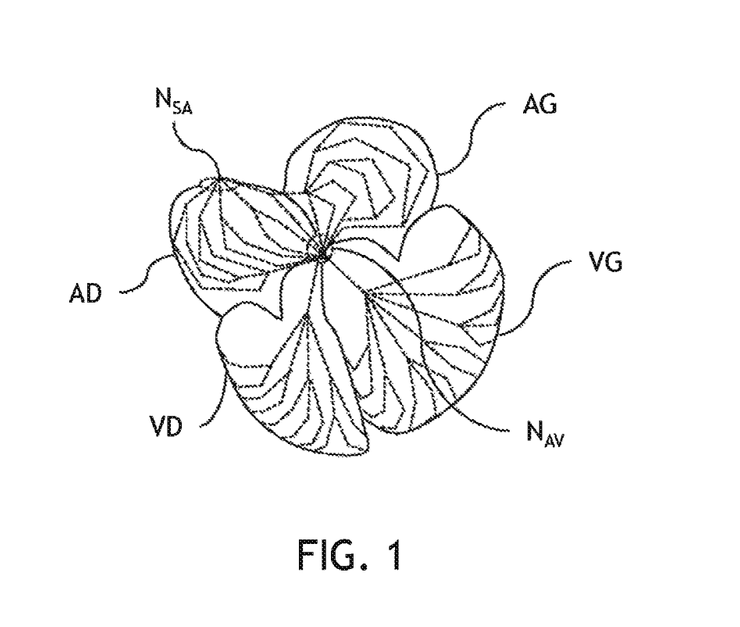
FIG. 1 is a diagram illustrating the propagation of the depolarization of the cells of a heart not suffering from cardiac arrhythmia.

In a heart that does not exhibit arrhythmia at a given instant (see FIG. 1), the cardiac contraction stems from a process of cyclical depolarization (reversal of the electrical polarity of the membrane of the cells which drives the activation thereof in order for them to fulfill their function, contraction in the case of the heart) of a group ($N_{SA}$) of cells situated in the upper part of the right atrium (OD) constituting the sinus node (or also called sino-atrial node). This depolarization is rapidly propagated in the manner of a wave in orderly fashion from top to bottom and incrementally to all the cells of the two right and left atria OD, OG, which triggers the quasi-synchronous contraction thereof. The propagation then takes place to the atrio-venticular node ($N_{AV}$) and then to the two right and left ventricles VD, VG, which then provokes the contraction thereof with a slight delay in relation to that of the atria. The propagation of the depolarization is orderly, and can be represented by rays leaving the sinus node which are in turn divided and so on then converge at the atrio-ventricular node from which other rays leave which are also divided and so on (see the dotted lines in FIG. 1).

Figure 2:
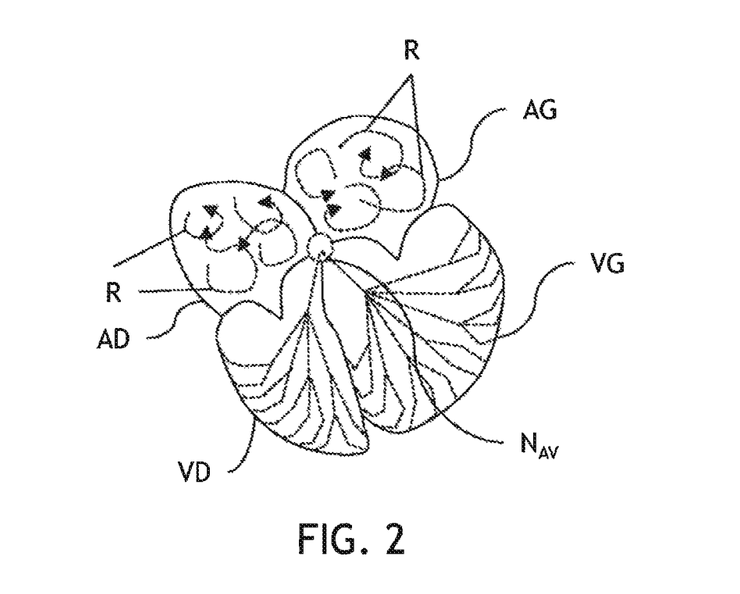
FIG. 2 is a diagram illustrating the propagation of the depolarization of the cells of a heart suffering from cardiac arrhythmia and exhibiting rotors R.

When there is atrial fibrillation (see FIG. 2), the propagation of the depolarization is no longer orderly and the depolarization is propagated within the atria OD, OG in a very rapid and disorganized manner.

The mechanisms initiating AF are now well known; they are most often extrasystoles generally originating from one or more of the pulmonary veins (in the left atrium). By contrast, the mechanisms responsible for the perpetuation of the AF are not well known (arythmogenic substrate).

There are a number of theories, but one of the most plausible is the rotor R theory. This involves a propagation of the depolarization which follows a loop-shaped path, involving reentries. Rotors can be more or less numerous and can be activated alternately.

The atrial fibrillation can also be due to focal sources, that is to say areas where the cells are hyperexcitable leading to a very rapid excitation frequency.

These rotors and focal sources have been recently documented in humans: Narayan et al., "*Treatment of atrial fibrillation by the ablation of localized sources: CONFIRM (Conventional ablation for atrial fibrillation with or without focal impulse and rotor modulation)trial*", (French title: "Traitement de la fibrillation atriale par l'ablation de sources localisées: CONFIRM (ablation conventionnelle pour la fibrillation atriale avec ou sans modulation d'impulsion focales ou de rotor)"), in *J. Am. Coll. Cardiol.*, 60, 628-636 (2012) and Haissaguerre et al., "*Driver domains in persistent atrial fibrillation*" (French title: "Zones motrices dans la fibrillation atriale persistante"), in *Circulation*, 12 Aug. 2014; 130(7): 530-8.

In order to treat AF, the areas suspected of contributing to this abnormal mechanism are ablated (the tissue of the suspected areas is destroyed, most commonly by radiofrequency, but any other energy source can be used). Several AF substrate ablation techniques have been proposed and there is as yet no consensus.

Moreover, different approaches for identifying tissues suspected of being responsible for the fibrillation have been perfected to guide the ablation.

A first approach for identifying the tissues suspected of being responsible for the AF is the detection of complex fractionated potentials (complex fractionated atrial electrograms, or even under the acronym CFAE) was developed by Dr Nademanee in 2004: K. Nademanee et al., "*A new approach for catheter ablation of atrial fibrillation: mapping of the electrophysiologic substrate*" (French title: "Une nouvelle approche pour l'ablation par cathéter dans la fibrillation atriale: cartographie du substrate électrophysiologique") in J. Am. Coll. Cardiol., 2 Jun. 2004; 43(11): 2044-53.

It is now strongly suspected that the CFAEs correspond to the electrical signals recorded on the sites of these rotors or of these focal sources. This approach makes it possible to stop the AF in 99% of cases and 95% of cases according to the publications: K. Nademanee, ibidem; J. Seitz et al., "Active or passive pulmonary vein in atrial fibrillation: is pulmonary vein isolation always essential?" (French title: "Veine pulmonaire active ou passive dans la fibrillation atriale: l'isolement de veines pulmonaires est-il toujours essentiel?"), in Heart Rhythm, April 2014; 11(4): 579-86. The technique developed by Dr Nademanee is also that which gives the best immediate and long term (published) results.

However, many CFAEs are said to be passive and the ablation thereof is pointless and/or ineffective, even deleterious. The active CFAEs can currently be discriminated from the passive CFAEs only by the visual analysis of expert operators. Unfortunately, the visual analysis of the CFAEs leads to low reproducibility because it is difficult for non-expert operators.

For that reason, automatic CFAE detection software packages have been developed (Biosense Webster and Saint Jude Medical). These software packages analyze the electrograms (EGMs) area by area in the atria. During the per-zone analysis period (2.5 sec for the Biosense Webster software), the times (generally in ms) between the deflections relative to the base line (electrograms) are measured. Several algorithms can then be implemented and the results displayed using a color code to guide the practitioners:

the SCI (Shortest Complex Interval) algorithm in which, for each area, the color displayed corresponds to the value of the duration of the shortest interval between two CFAEs recorded during the analysis time;

the ICL (Interval Confidence Level) algorithm in which, for each area, the color displayed corresponds to the number of intervals between two CFAEs recorded during the analysis time; and the ACI (Average Complex Interval) algorithm in which, for each area, the color displayed corresponds to the average value of the duration of all of the intervals between two CFAEs recorded during the analysis time.

Unfortunately, these software packages present a number of drawbacks including the following.

They use the definition of the term CFAE given by Dr Nademanee which does not sufficiently accurately define interesting fractionated electrical potentials which reflect the persistence of the arrhythmia, which leads to a high number of false positives, and ultimately to a high number of pointless ablations. In effect, with this analysis, only the measurement of the time between two electrical deflections (events) (also commonly called "cycles") is taken into account, without differentiating the duration of the electrograms and of the base lines.

The target interval detection thresholds are defined absolutely without taking into account the frequency (or the cycle) of the atrial fibrillation specific to each patient. The frequency of the atrial fibrillation has a direct influence on the fragmentation of the atrial electrical potentials (the faster the frequency, the more the potentials fragment): Konings et al., "*Configuration of unipolar atrial electrograms during electrically induced atrial fibrillation in humans*" (French title: "Configuration d'électrogrammes atriaux unipolaires pendant la fibrillation atriale induite électriquement chez l'Homme"), in *Circulation*, 1997; 95:1231-1241.

They do not take account of the existence or of the absence of a repetition of the events measured, from one beat to another.

They do not take into account, in the analysis of the electrograms, the potentials whose amplitude is above a given threshold. Taking account of the voltage (as Biosense Webster does) is important, but the elimination of a high-amplitude deflection in the analysis of the cycles can be problematic. In effect, it is sometimes possible to have potentials of amplitude above the given threshold which are interesting for the analysis of the electrogram.

Thus, these automatic methods which could have assisted more practitioners in identifying the areas of the heart to be ablated (arythmogenic substrate of the AF) are these days still not efficient enough.

Another mapping technique has been developed by Narayan et al., ("*Treatment of atrial fibrillation by the ablation of localized sources: CONFIRM (Conventional ablation for atrial fibrillation with or without focal impulse and rotor modulation) trial*, in *J. Am. Coll. Cardiol.*, 60, 628-636 (2012)). The purpose of the latter is to detect the rotors directly. The method consists of a simultaneous analysis in each of the atria by multi-electrode probes of large size (64 electrodes per atria) inserted using catheters and allowing a global or "panoramic" analysis of the two atria (and not regional) in order to detect the rotors and the focal sources.

The results obtained using these rotor and focal source locating maps are however deceptive. In effect, the above-mentioned article indicates a rate of 52% return to normal rhythm (also called sinus rhythm).

The low results of this method are possibly linked to the absence of precision in this global view but with little precision, the fact that the morphology of the electrical potentials (or electrograms) is not taken into account and the difficulty in reconstructing the electrical propagation in the case of fragmented potentials.

A more recent approach presented at two international conventions in 2014 (Seitz and Bars, Heart Rhythm Society 2014 in San Francisco & ISCAT 2014 in Paris) consists in performing a regional visual mapping using a multi-electrode probe. This approach allows for an analysis of the fragmentation and of the activation in order to detect the rotors and their slow underlying conduction. This technique gives very good results with 96% stoppage of AF and a good reproducibility rate (7 operators).

Unfortunately, the analysis according to this method is a visual analysis whose results depend on the operator.

SUMMARY OF THE INVENTION

One aim of the invention is therefore to mitigate at least one of the drawbacks of the prior art mentioned above.

In particular, one aim of the invention is to propose a method for identifying the areas of the heart likely to be involved in the perpetuation of atrial fibrillation (AF) more reliably than is currently possible, in order to assist the practitioner in his or her choice of treatment.

For that, the invention proposes a method for identifying areas of the heart of a patient likely to be involved in the perpetuation of atrial fibrillation, hereinafter target areas, from a plurality of local recordings made on the heart of the patient during a measurement window, each local recording corresponding to an area of the heart of the patient, each local recording comprising at least one local electrogram and possibly at least one base line, the method comprising the following steps:

the obtention of a reference cycle of the arrhythmia, the reference cycle being the average duration of the base lines between two local electrograms of a local recording corresponding to a healthy area of the heart of the patient; and for each local recording:

the determination of base lines between two local electrograms;

the calculation of at least ratio out of:

an average ratio of the duration of the base line to the reference cycle of the arrhythmia;

a median ratio of the duration of the base line to the reference cycle of the arrhythmia;

for each base line, a ratio of the duration of the base line to the reference cycle of the arrhythmia;

the classification of the corresponding area of the heart according to its degree of involvement in the perpetuation of the AF, the degree of involvement of the area being a function of the ratio or ratios calculated.

This invention allows for a fine analysis of the electrical signals in order to determine the sources targeted by the ablation through a quantification of the percentage of the reference cycle of the AF recorded in different regions of the atria. Taking into account the reference cycle of the AF makes it possible to overcome many of the problems described above.

In addition, an area can be classified as a non-target area if the average ratio, the median ratio, or all the ratios calculated for the base lines of the corresponding local recording is/are greater than or equal to a first value, the area otherwise being classified as a true or false positive target area.

In addition or alternatively, an area can be classified as a true or false positive priority target area if the average ratio, the median ratio, or at least one ratio calculated for a base line of the corresponding local recording is less than or equal to a second value, if necessary less than the first value.

In addition or alternatively, an area can be classified as a true or false positive secondary target area if the average ratio, the median ratio, or at least one ratio calculated for a base line of the corresponding local recording lies between the second value and a third value lying between the first and second values; and classified as a true or false fertiary positive target area if the average ratio, the median ratio, or at least one ratio calculated for a base line of the corresponding local recording lies between the third value and the first value.

In addition or alternatively, the classification of each of the areas of the heart can be performed according to one of the following modalities:
  it is also a function of the repetition in the corresponding local recording of the base lines with calculated ratio of repetitive values; a target area being a true positive if the repetition corresponding to the ratio value having led to the classification of the area as being a target area is proven;
  it is also a function of the average of the amplitude values of the depolarizations of the corresponding local recording; a target area being a true positive if the average of the amplitude values is less than a given threshold value;
  it is also a function of the repetition in the corresponding local recording of the base lines with calculated ratio of repetitive values and a function of the average of the amplitude values of the depolarizations of the corresponding local recording; a target area being a true positive if the repetition is proven and if the average of the amplitude values is greater than a given threshold value.

In addition or alternatively, the method can comprise, for at least some of the local recordings of the heart:
  the obtention of at least one regional recording from a plurality of local recordings corresponding to adjacent areas, the adjacent areas forming a region corresponding to the regional recording, the local recordings not exhibiting any identifiable base line being discarded, so the regional recording comprises at least one regional electrogram; and
  for each regional recording:
    the determination of base lines between two regional electrograms;
    the calculation of at least one ratio out of:
      an average ratio of the duration of the base line to the reference cycle of the arrhythmia; and
      for each base line, a ratio of the duration of the base line to the reference cycle of the arrhythmia;
    the classification of the corresponding region of the heart according to its degree of involvement in the perpetuation of the AF, the degree of involvement of the region being a function of the ratio or ratios calculated;
the other steps of the method being carried out by replacing:
  local recording by regional recording and
  area by region.

This last modality corresponds to a multitrack analysis, that is to say the analysis is done in concrete terms on several recordings (each being recorded on a track) at the same time.

In another aspect of the invention, the latter proposes carrying out the multitrack analysis without involving single-track analysis, but still by taking into account the ratio. This is reflected by a method for identifying regions of the heart of a patient likely to be involved in the perpetuation of atrial fibrillation, hereinafter target regions, from a plurality of regional recordings made on the heart of the patient during a measurement window, each regional recording corresponding to a region of the heart of the patient combining a plurality of areas, the method comprising the following steps:
  the obtention of a reference cycle of the arrhythmia, the reference cycle being the average duration of the base lines between two depolarizations of a local recording corresponding to a healthy area of the heart of the patient; and
  for each regional recording:
    the determination of base lines between the depolarizations of the regional recordings during the measurement window;
    the calculation of at least one ratio out of:
      an average ratio of the duration of the base line to the reference cycle of the arrhythmia;
      for each base line, a ratio of the duration of the base line to the reference cycle of the arrhythmia;
    the classification of the corresponding region of the heart according to its degree of involvement in the perpetuation of the AF, the degree of involvement of the region being a function of the ratio or ratios calculated.

In addition, a region can be classified as a non-target region if the average ratio or if all the ratios calculated for the base lines of the corresponding regional recording is/are greater than or equal to a first value, the region otherwise being classified as a true or false positive target region.

In addition or alternatively, a region can be classified as a true or false positive priority target region if the average ratio or at least one ratio calculated for a base line of the corresponding regional recording is less than or equal to a second value, if necessary less than the first value.

In addition or alternatively, a region can be classified as a true or false positive secondary target region if the average ratio or at least one ratio calculated for a base line of the corresponding regional recording lies between the second value and a third value lying between the first and second values; and as a true or false positive tertiary target region if the average ratio or at least one ratio calculated for a base line of the corresponding regional recording lies between the third value and the first value.

In addition or alternatively, the classification of each of the regions of the heart can be performed according to one of the following modalities:
  it is also a function of the repetition in the corresponding regional recording of the base lines with calculated ratio of repetitive values; a target region being a true positive if the repetition is proven;
  it is also a function of the average of the amplitude values of the depolarizations of the corresponding regional recording; a target region being a true positive if the average of the amplitude values is less than a given threshold value;
  it is also a function of the repetition in the corresponding regional recording of the calculated ratio base lines of repetitive values and a function of the average of the amplitude values of the depolarizations of the corresponding regional recording; a target region being a true positive if the repetition is proven and if the average of the amplitude values is greater than a given threshold value.

According to another aspect of the invention, an apparatus is proposed for identifying areas of the heart likely to be involved in the perpetuation of atrial fibrillation, comprising a digital analyzer and a digital mapper,
the digital analyzer being capable of implementing the method described above;
the digital mapper being capable of generating a map of the heart of the patient on which the classification of the areas of the heart is formed.

The steps of the method described above can be implemented by a computer program comprising a series of instructions when the latter are executed by a processor.

This computer program can be stored on a non-transient and computer-readable storage medium.

SUMMARY OF THE DRAWINGS

Other aims, features and advantages will become apparent on reading the following detailed description with reference to the drawings given in an illustrative and nonlimiting manner, in which.

DETAILED DESCRIPTION

Single-Track Analysis

The present description will involve recordings of the electrical activity (potential) of an area of the heart placed between two electrodes (or dipole) during a measurement window. The electrical activity of the heart is manifested by one or more depolarizations relative to a base line. Thus, a recording is generally represented by a continuous line describing depolarizations, that is to say deflections from the base line, the base of which is more or less wide and the amplitude of which is more or less high (see FIG. 4). Between two depolarizations there is generally a portion fluctuating only slightly. Such a portion is the base line. The depolarizations relative to the base line will be called "electrograms" or EGM. In the case where a duration less than 35 ms, preferentially 30 ms, separates two depolarizations, these two depolarizations are then considered, for the analysis, as a succession of depolarizations which belong to one and the same EGM.

The recording can be the series of raw measurements, that is to say as obtained without processing during or after the measurement. The recording is preferably the series of measurements previously processed, either during or after the performance of the measurements, in order in particular to eliminate the noise due in particular to the equipment present in the room, even in the vicinity of the room where the recordings are made. In practice, the electrical activity of the heart is measured using a pair of electrodes (also called dipole) covering the corresponding area. To simplify the understanding of all of the present description, the local recordings will be distinguished from the regional recordings. A local recording is obtained by measurement, notably using a dipole. A regional recording is obtained by the addition or subtraction of a plurality of local recordings corresponding to adjacent areas of the heart forming a region (refer to the multitrack analysis described later). Similarly, the local EGMs will be distinguished from the regional EGMs. A local EGM is an EGM of a local recording, whereas a regional EGM is an EGM of a regional recording.

Figure 3:
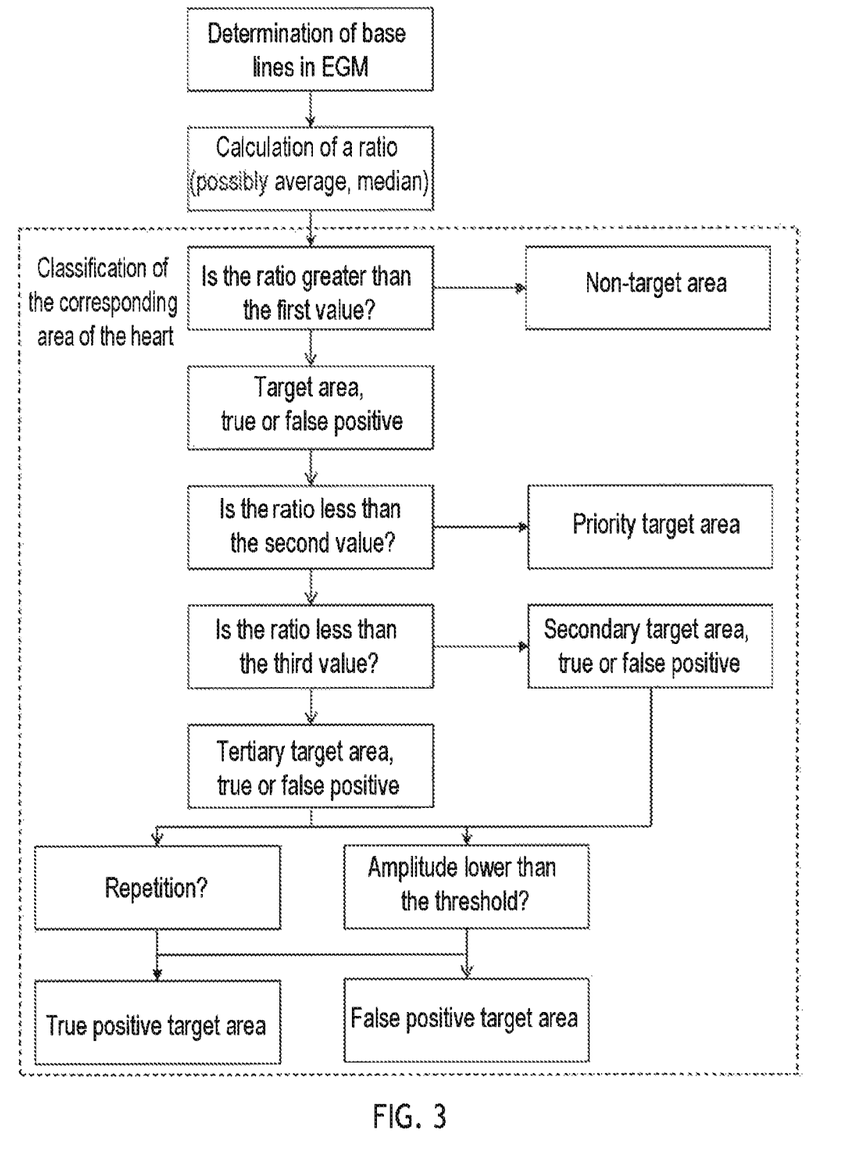
FIG. 3 schematically represents the steps of the method according to the invention.

Referring to FIG. 3, a method for identifying areas of the heart likely to be involved in the perpetuation of AF (also called cardiac arrhythmia) according to the invention is described hereinbelow. In a preferred embodiment, the method is performed on one of the atria of the heart or on both (right and left).

The method is carried out from a plurality of local recordings performed on the heart of the patient during a measurement, each recording corresponding to an area of the heart of the patient. Each local recording comprises at least one local EGM. It can moreover also exhibit at least one base line.

The measurement window is a time window of a determined duration and chosen to be long enough to be able to record several cycles of the arrhythmia (for example more than two reference cycles of the arrhythmia). The measurement window is advantageously greater than 2 s, preferably greater than or equal to 2.5 s. The measurement window is either temporally continuous, or temporally discontinuous. Thus, the measurement window can also be two time periods which together have a duration advantageously greater than 2 s, preferably greater than or equal to 2.5 s during which the measurements are performed on the same area of the heart. The measurements can be repeated in each area to improve the accuracy.

The measurement window is of course the same for all the local or regional recordings considered both in terms of duration and in terms of measurement instant.

More practically, it is possible to consider a portion as base line if, over the entire portion, the value of the electrical potential measured is below a lower threshold value which generally is equal to at least the maximum level of noise observed (notably measured beforehand) for the equipment and its environment, and is advantageously equal to the maximum noise observed augmented by 0.01 mV. The lower threshold value preferably lies between 0.02 mV and 0.04 mV, still preferably approximately 0.02 mV. The depolarizations can be isolated (generally corresponding to a normal electrical activity of a "healthy" tissue, in other words these are non-fragmented potentials) or grouped together with no base line inserted between them (complex activities with several peaks). Thus, a base line begins at the end of a depolarization and ends at the start of another subsequent depolarization.

Figure 4:
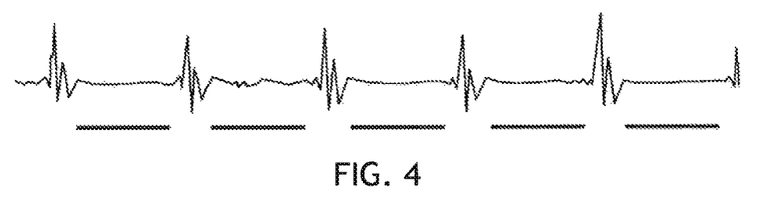
FIG. 4 shows an example of electrogram in a healthy area (non-complex narrow and ample depolarizations)

More specifically, a local recording measured in a healthy area exhibits a succession of cycles made up of a basal activity represented by a base line fluctuating very slightly, the duration of which is generally greater than 120 ms, followed by a strong activity (EGM) leading to a strong and brief change of amplitude (depolarization) of the measured potential (the duration is generally less than 40 ms) (FIG. 4). The duration of the cycles is substantially constant.

On the other hand, some recordings may exhibit a form moving away from the form of a healthy local recording.

These recordings, of abnormal form, exhibit a fractionation of the depolarizations, in fact they show at least one EGM comprising more than three depolarizations which follow rapidly (generally in a time of between 2 and 35 ms) with no identifiable intermediate base line, these non-isolated depolarizations are also of lower amplitude. This type of EGM is called complex fractionated atrial EGM (also known by the acronym CFAE).

However, although the CFAEs are the signal of an abnormal event in the electrical activity of the heart, they in no way prejudge the active or passive nature of the corresponding area of the heart in the perpetuation of AF.

Figure 5:
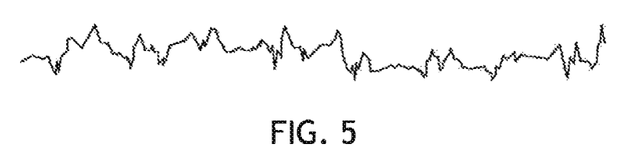
FIG. 5 shows an example of complex electrogram corresponding to a continuous CFAE, that is to say not having an identifiable base line.
Figure 8:
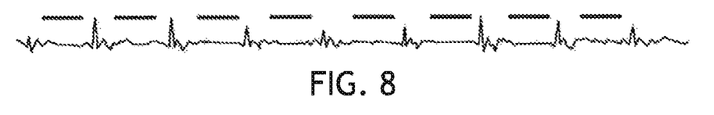
FIG. 8 shows an example of non-fragmented electrogram with a base line of a duration less than the reference cycle of the arrhythmia (called "rapid fire")

Two types of so-called active CFAEs can be distinguished:
the CFAE train which is a succession of CFAEs having a duration greater than or equal to 50 ms (FIG. 6); and
the continuous CFAE which is a succession of depolarizations with a virtual absence of base line (FIG. 5).
Other recordings may show EGMs resembling healthy depolarizations but between which the duration of the base line is constantly short, generally less than 120 ms (FIG. 8). The amplitude of the potentials measured is generally less than that of the potentials measured for healthy depolarizations; they are not fragmented and their width is generally less than 35 ms. These EGMs are called rapid fire EGMs, or more commonly rapid fires.

The measurements can be obtained in different ways known to those skilled in the art. For example, they are obtained by inserting a pair of electrodes into the body of the patient, to an area of the heart of interest to the practitioner, the electrical activity of this area is recorded during the selected time window. The location of the area is also recorded. At the end of the time window, the pair of electrodes is moved to another area of the heart of interest to the practitioner, and the recording is performed on this other area. This is repeated over a plurality of areas of the heart forming a meshing of the heart.

Alternatively, the recording can be performed using a multi-electrode probe comprising a plurality of pairs of electrodes allowing the electrical activity of a plurality of areas of the heart to be recorded at the same time. This allows for a faster and more accurate recording of all the areas of the heart as well as a simultaneous recording of several areas (allowing the creation of a regional EGM) that are of interest for the practitioner. Moreover, since the measurement time is reduced, it is then possible to obtain a finer meshing of the heart.

The recordings can be used directly after measurement or stored pending analysis by the present method.

The particular feature of the present method is to take account of the reference cycle of the arrhythmia measured over one or more local recordings performed on the patient in order to analyze the local recordings of this patient relative to this cycle. This is why the method comprises the obtention of a reference cycle of the arrhythmia of the patient.

The reference cycle of the arrhythmia is the average duration of the base lines between two local EGMs of a local recording corresponding to a healthy area of the heart of the patient. Advantageously, the reference cycle of the arrhythmia is determined from base lines taken at least two different moments in a local recording corresponding to a "healthy" area of the heart, that is to say an area exhibiting a voltage of amplitude of at least 0.5 mV with simple potentials (normal depolarization of the membrane of the cells forming the tissue of the area) whose duration, generally, does not exceed 40 ms. In these healthy areas, the depolarizations are highly instantaneous (their duration is generally less than 40 ms) such that the duration of the base line exhibits a great correlation with the total cycle of the electrical activity of the tissue, hence the use of the term cycle. The reference cycle of the arrhythmia is measured on the right atrium, the left atrium or the coronary sinus of the patient being in atrial fibrillation (spontaneous or intentionally triggered if necessary). Most often, this reference cycle is measured in the left auricle (smallest pocket in the left atrium whose activity is generally healthy).

The reference cycle of the arrhythmia is preferably the average (for example of at least 10 cycles, even 20 cycles) of the base line durations in one or more healthy local recordings.

Generally, the reference cycle of the arrhythmia differs from one patient to another. Moreover, its duration depends on the complexity of the arrhythmia, on the more or less pathological state of the atria and on the presence of anti-arrhythmia drugs. Generally, the reference cycle of the arrhythmia lies between approximately 110 ms and approximately 400 ms (generally between approximately 140 ms and approximately 220 ms).

The measurement window is advantageously chosen in such a way as to allow the observation of at least two, preferably more than two, EGMs in the local recording corresponding to two reference cycles of the arrhythmia (that is to say that their durations are equivalent from a medical point of view).

The method also comprises, for each local recording, the determination of base lines between two local EGMs and the calculation of at least one ratio relative to the reference cycle of the arrhythmia:
for each base line, calculation of the ratio of the duration of the base line to the reference cycle of the arrhythmia (which means that, if this option is chosen, a ratio is calculated for each identified base line);
an average ratio of the duration of the base line to the reference cycle of the arrhythmia;
a median ratio of the duration of the base line to the reference cycle of the arrhythmia.

Thus, the method according to the present invention rests on the calculation of a ratio whose denominator is the reference cycle of the arrhythmia, thus culminating in an automatic quantification of this ratio.

The method also comprises the classification of each of the areas according to their degree of involvement in the perpetuation of the AF. The degree of involvement of an area is a function of the ratio or ratios calculated for the corresponding local recording.

The method finally comprises the identification, from the classification, of the target areas.

The areas can be classified according to different scales of degree of involvement. These scales can be more or less fine.

For example, an area is classified as a non-target area if the average ratio or all the ratios calculated for the base lines of the corresponding local recording are greater than a first value, and a target area, true or false positive, otherwise.

Figure 6:
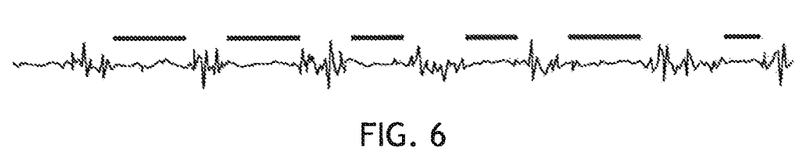
FIG. 6 shows an example of repetitive, non-continuous fragmented electrogram (called "CFAE train") with a succession of base lines of duration less than the reference cycle of the arrhythmia in a repetitive (non-isolated) manner.
Figure 7:
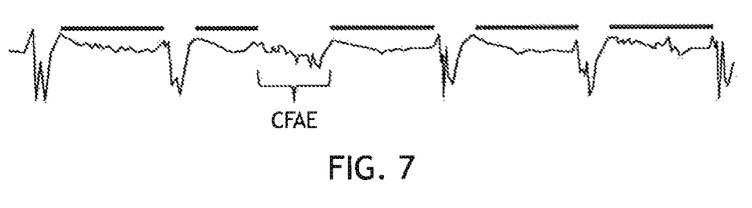
FIG. 7 shows an example of fragmented electrograms with short base lines (therefore with long depolarization event duration) but in an isolated manner (without temporal stability)

In other words, the corresponding non-target area has a low degree of involvement and is a passive area with respect to the arrhythmia. The true or false positive target areas generally exhibit local recordings with CFAEs (continuous or "CFAE trains") or rapid fires if non-fragmented (FIGS. 5, 6 and 8 respectively).

As another example, an area is classified as a true or false positive priority target area if the average ratio or at least one ratio calculated for a base line of the corresponding local EGM is less than or equal to a second value, if necessary less than the first value.

In other words, if no base line is identifiable in a local recording (zero calculated ratio), or if the calculated ratio is low (for example less than 35%), the corresponding area has a very high degree of involvement in the perpetuation of the AF (see FIG. 5). In effect, such an area is probably an area of slow conduction (substrate of the rotors), potentially the seat of a rotor or at least a part thereof, which corresponds to a priority target area. A rotor or even reentry characterizes a phenomenon in which the electrical depolarization, which is normally propagated from one area of the heart to another so as to allow the latter to beat (as described above in the introduction), is propagated in a loop forming an electrical circuit. This electrical circuit sustains itself thus perpetuating the arrhythmia. For such a phenomenon to occur, a slowdown of electrical conduction (slow conduction) is necessary.

In the case where the first and second values are used, the areas in which the calculated ratio lies between these two values are classified as true or false positive target areas.

In other words, the corresponding area has a high average degree of involvement.

As another example, the classification can be further refined. For that, an area is classified as a true or false positive secondary target area if:
 the average ratio, the median ratio, or none of the ratios calculated for the base lines of the corresponding local recording is less than the second value; and
 the average ratio, the median ratio, or at least one ratio calculated for a base line of the corresponding local recording lies between the second value and a third value lying between the first and second values.

The area is then classified as a true or false positive tertiary target area if:
 the average ratio, the median ratio, or none of the ratios calculated for the base lines of the corresponding local recording is less than the second value;
 the average ratio, the median ratio, or at least one ratio calculated for a base line of the corresponding local recording lies between the third value and the first value.

The numeric values of the first, second and third values are chosen according to the needs, of the patient, of the measurement circumstances, etc. Advantageously, the values for the above examples are:

| First value | Second value | Third value |
|---|---|---|
| 65% | 35% | 50% |

Nevertheless, these values are indicative only and the practitioner will be able to decide on other values depending on the case.

Thus, preferentially, the classification comprises at least four basic levels: priority targets, secondary targets, tertiary targets and non-targets (increasingly less high degrees of involvement). Each of these levels can be subdivided. There are not necessarily identical numbers of subdivisions of the basic levels.

The priority target areas (of very high degree of involvement) are areas that would need to be ablated as a priority because suspected of being areas responsible for the perpetuation of the AF.

Thus, the probability for them to be responsible for the perpetuation of the AF is extremely strong.

The secondary and tertiary target areas (of high to medium degree of involvement) are areas possibly to be ablated, the practitioner chooses whether or not to do so, notably as a function of the result of the ablation of the priority targets, but their classification indicates a strong to medium suspicion of responsibility in the perpetuation and/or initiation of the cardiac arrhythmias. Thus, the probability for them to be responsible for the perpetuation of the AF is strong to medium.

The non-target areas are areas of low degree of involvement are areas which should not be ablated because the probability for them to be responsible for the perpetuation of the AF is extremely low.

The reliability of the method can be enhanced by additional criteria with the following steps. These steps make it possible to differentiate the true and the false positives of the target areas.

In a first variant, the classification of each of the areas of the heart is also a function of the repetition in the corresponding local recording of the base lines with calculated ratio of repetitive values; a target area being a true positive if the repetition is proven.

The term repetitive means that the durations of the base lines are equal to plus or minus 15%, preferentially 10%, more preferentially 5% relative to one another.

In other words, there is a temporal stability in the occurrence of the abnormal events (abnormal local EGMs) in the corresponding local recording. It is this temporal stability which makes it possible to specify the classification. This temporal stability is preferentially maintained for at least 3 successive base lines, (preferentially at least 4 or even at least 5 successive base lines). The false positive target areas then change to non-target areas.

In another variant, the classification of each of the areas of the heart is also a function of the average of the amplitude values (or "voltage") of the depolarizations of the corresponding local recording; a target area being a true positive if the average of the amplitude values is less than a given threshold value (generally 0.6 mV) and false positive otherwise. The false positive target areas then change to non-target areas.

The above two variants can advantageously be combined. In this case, the classification of each of the areas of the heart is also a function of the repetition in the corresponding local recording of the base lines with calculated ratios of repetitive values and of the average of the amplitude values of the depolarizations of the corresponding local EGM;

a target area being a true positive if the repetition is proven and if the average of the amplitude values is less than a given threshold value, it is a false positive otherwise. The false positive target areas then change to non-target areas.

Moreover, the method can also take into account the duration of the local EGMs in order in particular to distinguish the CFAE trains and rapid fires. For that, the classification is also a function of the duration of the durations of the local EGMs, notably those of the recordings corresponding to true or false positive target areas, whether they are priority, secondary or tertiary. If the duration of the EGM is less than a given local EGM threshold duration, the EGM is classified as rapid fire; otherwise, the local EGM is classified as CFAE train. The given local EGM threshold duration is generally chosen to be less than 45 ms, preferentially less than 35 ms, still preferentially less than 30 ms. The distinction of the CFAE trains and the rapid fires can be useful, notably for research purposes. The method also comprises the forming of the classification on a map of the heart of the patient. The forming comprises all the possible methods for representation of the degrees of involvement of the areas on a map of the atria of the patient, for example two degrees of involvement may differ by two different colors, two different shades of one and the same color, two different patterns, even by dynamic means such as the presence or not of blinking, the frequency of the blinking, etc.

The method can also comprise a step of displaying of the map of the atria thus obtained. The map of the atria displayed can show all the areas of the atria for which the electrical activity has been measured or only some of them. For example, it is possible to choose to display only the areas of very high degree of involvement, or the areas of high degree of involvement, or the areas of low degree of involvement, or a mix thereof.

Hereinabove, the method corresponds to a single-track analysis, that is to say that the local recordings are classified individually.

Multitrack Analysis

Although a single-track analysis gives satisfactory results, these can be further enhanced using a multi-track analysis described hereinbelow, notably with respect to the areas classified as non-target by the single-track analysis.

A multi-track analysis consists primarily in identifying regions of the heart where rotors occur. In effect, it may be that, upon the single-track analysis of the areas of a region, no area is classified as target whether true or false positive because the calculated ratio is greater than the first value, whereas in reality, because of the presence of a rotor, all of the events indicating the AF are distributed over a region combining several adjacent areas.

In order to take account of this possibility, the method can comprise the generation of at least one regional recording from a plurality of local recordings corresponding to adjacent areas (see FIG. 9), notably by addition of the plurality of local recordings (or subtraction of the corresponding base lines). The adjacent areas then form a region corresponding to the regional recording.

The term "addition(add)" should be understood here to mean the act of adding the measurements corresponding to the local recordings concerned or the act of superimposing the local recordings concerned on one another.

Figure 9:
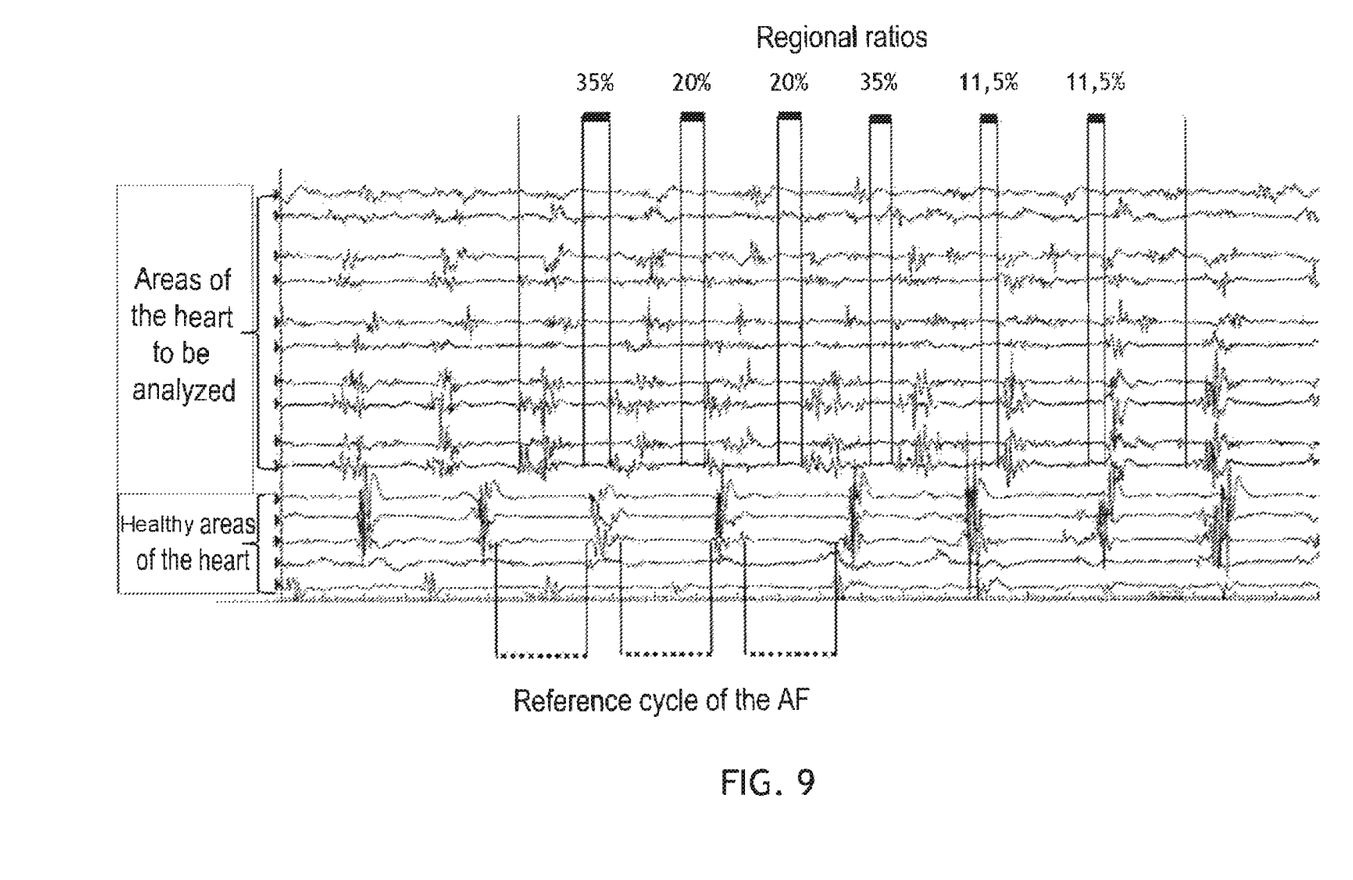
FIG. 9 shows a set of local electrograms corresponding to a region of the heart of the patient from which a regional electrogram can be obtained.

Thus, as can be seen in FIG. 9, when the local recordings are added to generate a regional recording, regional EGMs are obtained formed from at least one local EGM (in the case of a plurality of local EGMs, each local EGM lies on a local recording distinct from another). Thus, these regional EGMs exhibit a duration greater than or equal to the duration of the local EGMs.

The base lines obtained for this regional recording are analyzed in relation to the reference cycle of the arrhythmia. However, it must be specified that the local recordings not exhibiting any identifiable base line must be discarded (the corresponding areas are priority target areas following the single-track analysis). The rest of the explanation takes this last comment into account.

The method is then carried out by substituting the local recordings with the regional recordings. In other words:

for each regional recording, the method comprises:
   the determination of base lines between two depolarizations in the regional recording;
   the calculation of at least one ratio out of:
      a ratio of the duration of the base line to the reference cycle of the arrhythmia for each base line;
      an average or median ratio of the duration of the base line to the reference cycle of the arrhythmia; and
   the classification of the corresponding region of the heart according to its degree of involvement in the perpetuation of the AF, the degree of involvement of the region being a function of the ratio or ratios calculated.

This also includes the case where no regional recording is really obtained by addition of the local recordings (or subtraction of the base lines) of the corresponding areas, but only by determining, in the local recordings, a portion in which all the local recordings of areas of the region exhibit a part or all of a base line.

The other steps described above are also applicable here for the regional recordings. For that, it is sufficient to substitute the local recordings with the regional recordings and the areas of the heart with the regions of the heart.

Moreover, the method can be carried out by saving the calculations on the local recordings. In other words, the steps of the method are carried out only from the regional recordings.

Such a method is therefore a method for identifying regions of the heart of a patient likely to be involved in the perpetuation of atrial fibrillation, hereinafter target regions. The method starts from a plurality of regional recordings performed on the heart of the patient during a measurement window, each regional recording corresponding to a region of the heart of the patient, the method comprising the following steps:

the obtention of a reference cycle of the arrhythmia, the reference cycle being the average duration of the base lines between two depolarizations of a local recording corresponding to a healthy area of the heart of the patient; and for each regional recording:
   the determination of base lines between two depolarizations in the regional recording;
   the calculation of at least one ratio out of:
      an average ratio of the duration of the base line to the reference cycle of the arrhythmia;
      for each base line, a ratio of the duration of the base line to the reference cycle of the arrhythmia;
   the classification of the corresponding region of the heart according to its degree of involvement in the perpetuation of the AF, the degree of involvement of the region being a function of the ratio or ratios calculated.

Herein again, the regional recording is obtained by addition of local recordings (or subtraction of corresponding base lines) of the areas of the heart in the given region, bearing in mind that the local recordings not exhibiting any identifiable base line must be discarded (because they correspond to priority target areas, see explanation in the single-track analysis part).

Here too, the other steps described above are also applicable here for the regional recordings. For that, it is sufficient to substitute the local recordings with the regional recordings and the areas of the heart with the regions of the heart.

Advantageously, the grouping together of the areas by regions is performed in such a way that a region comprises a plurality of adjacent areas, generally at least 5 areas, preferably at least 10 areas, even more preferably between 20 and 50 areas.

In such a case, two areas are separated by a distance of at least 4 mm, preferably less than 2 mm, the distance being taken between the centers of the areas.

Preferably, a multi-track analysis is performed when the measurements have been recorded with a multi-electrode probe. In this case, it is possible and easy to consider that the extent covered by the electrodes of the multi-electrode probe constitutes a region whose surface area is preferentially of the order of 7 cm$^2$.

The regional recording can be generated over any measurement window but also over a portion thereof. In other words, it is the first depolarization preceded by a base line subsequent to the depolarization followed by a base line on the first local recording which is identifiable out of all the local recordings of the areas of the region.

The method also takes account of the delay between two different EGMs, in effect, the latter is a function of the distance between the two dipoles (each dipole allowing the measurement of an EGM of an area). The calculation of the ratio will then be matched to this delay. Moreover, it is preferable, but not necessary, for the distance between two areas of a same region not to exceed approximately 2 cm, even 3 cm.

If a probe of large surface area were used, a formula would have to adapt the limit priority target ratio to the distance.

In practice, given that these reentries are unstable and therefore locally mobile in a region, if the surface area of the probe does not exceed 7 cm$^2$ there is no need to weight the calculation of the ratio of the regional EGM as a function of the distance between the electrode dipoles.

Apparatus

Figure 10:
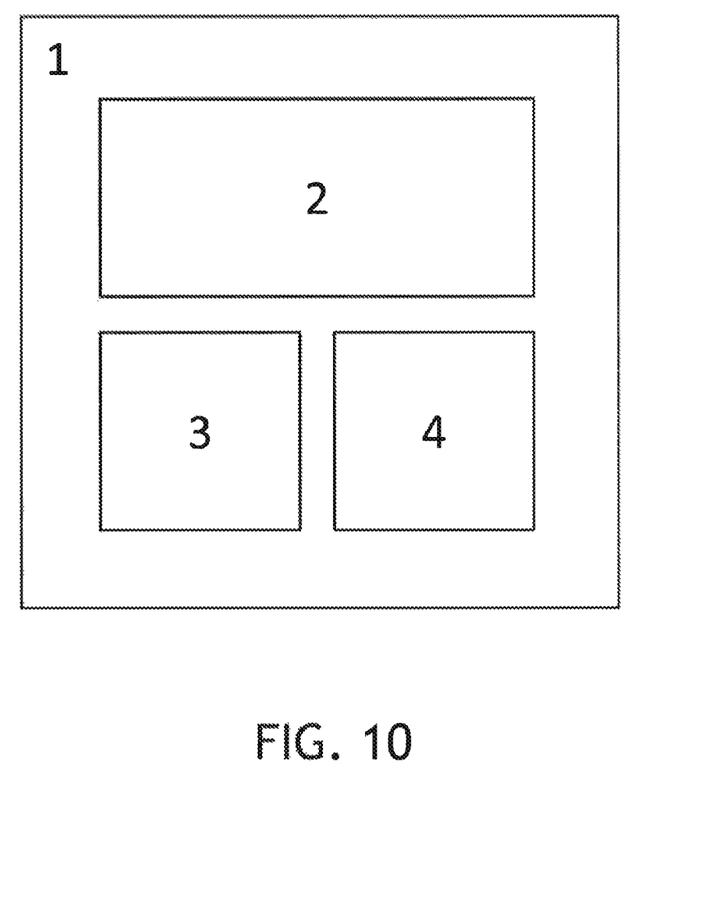
FIG. 10 schematically illustrates an apparatus for identifying areas of the heart likely to be involved in a cardiac arrhythmia according to the invention.

Referring to FIG. 10, an apparatus 1 for identifying areas of the heart likely to be involved in a cardiac arrhythmia is described hereinbelow. This apparatus 1 is capable of implementing the method described above.

This apparatus 1 comprises a digital analyzer 2 and a digital mapper 3.

The digital analyzer 2 is capable of receiving:
a reference cycle of the arrhythmia, the reference cycle being the average duration of the base lines between two depolarizations of a local EGM corresponding to a healthy area of the heart of the patient; and
a plurality of local EGMs or EGMs performed on the heart of the patient during a measurement window, each local EGM corresponding to an area of the heart of the patient.

For that, the digital analyzer 2 can comprise a reception module.

The digital analyzer 2 can be capable of generating regional EGMs from a plurality of local EGMs corresponding to adjacent areas of the heart. For that, the digital analyzer 2 can comprise a regional EGM generator.

The digital analyzer 2 is also capable of determining base lines between two depolarizations in a local and possibly regional EGM.

The digital analyzer 2 is also capable, for a local or regional EGM, of calculating at least one ratio out of:
an average ratio of the duration of the base line to the reference cycle of the arrhythmia;
for each base line, a ratio of the duration of the base line to the reference cycle of the arrhythmia.

For that, the digital analyzer 2 can comprise a computer.

The digital analyzer 2 is also capable, for a local or regional EGM, of classifying the corresponding area or region of the heart according to its degree of involvement in the perpetuation of the AF, the degree of involvement of the area or region being a function of the ratio or ratios calculated. The details of the classification are described above in the part describing the method. To perform the classification, the digital analyzer 2 can comprise a classifier.

The digital mapper 3 is capable of generating a map of the heart of the patient on which the classification of the areas or regions of the heart is formed.

The apparatus further comprises a display 4 for displaying the map of the heart of the patient.

Computer Program

The method described above can be implemented by a computer program. This computer program comprises a series of instructions which implement the steps of the method described above when they are executed by a processor.

This computer program can be stored on a non-transient and computer-readable storage medium. This type of storage medium can for example be a CD, a DVD, a USB key, a SIM card, etc.

The invention claimed is:

1. A method for identifying target areas of a heart of a patient likely to be involved in a perpetuation of atrial fibrillation (AF), comprising:
taking a plurality of local recordings of the heart of the patient during a measurement window, each local recording corresponding to an area of the heart of the patient, each local recording comprising at least two local electrograms (EGMs) and at least two base lines, the method further comprising
obtaining a reference cycle of an arrhythmia, the reference cycle being an average duration of a first reference base line and a second reference base line between a first local reference EGM and a second local reference EGM of a local recording corresponding to a healthy area of the heart of the patient, and
for each local recording:
determining an average duration of a first base line and a second base line between a first local EGM and a second local EGM;
calculating at least one ratio out of:
an average ratio of the average duration of the first base line and the second base line to the reference cycle of the arrhythmia;
a median ratio of the average duration of the first base line and the second base line to the reference cycle of the arrhythmia;
for each base line, a ratio of the duration of the base line to the reference cycle of the arrhythmia;
classifying the corresponding area of the heart according to the corresponding area's degree of involvement in the perpetuation of the AF, the degree of involvement of the area being a function of the ratio or ratios calculated; and generating and displaying a map of the heart of the patient on which the classified areas of the heart are formed.

2. The method as claimed in claim 1, in which an area is classified as a non-target area if the average ratio, the median ratio, or all the ratios calculated are greater than or equal to a first value,
the area otherwise being classified as a true or a false positive target area.

3. The method as claimed in claim 2, in which an area is classified as true or a false positive priority target area if the average ratio, the median ratio, or at least one ratio calculated f is less than or equal to a second value.

4. The method as claimed in claim 3, in which an area is classified as a true or a false positive secondary target area if the average ratio, the median ratio, or at least one ratio calculated lies between the second value and a third value lying between the first and second values; and
the area is classified as a true or false positive tertiary target area if the average ratio, the median ratio, or at least one ratio calculated lies between the third value and the first value.

5. The method as claimed in claim 1, in which the classification of each of the areas of the heart is also a function of a repetition in the corresponding local recording of the calculated ratio base lines of repetitive values;
a target area being a true positive if the repetition corresponding to the ratio value having led to the classification of the area as being a target area is proven.

6. The method as claimed in claim 1, in which the classification of each area of the heart is also a function of an average of amplitude values of depolarizations of the corresponding local recording;
a target area being a true positive if the average of the amplitude values is less than a given threshold value.

7. The method as claimed in claim 1, in which the classification of each of the areas of the heart is also a function of a repetition in the corresponding local recording of the base lines with calculated ratio of repetitive values and a function of an average of amplitude values of depolarizations of the corresponding local recording;
a target area being a true positive if the repetition is proven and if the average of the amplitude values is greater than a given threshold value.

8. The method as claimed in claim 1, further comprising, for at least some of the local recordings of the heart:
obtaining at least one regional recording from a plurality of local recordings corresponding to adjacent areas, the adjacent areas forming a region corresponding to the regional recording, the local recordings not exhibiting any identifiable base line being discarded, so the regional recording comprises at least one regional EGM; and
for each regional recording:
determining an average duration of a first regional base line and a second regional base line between a first regional EGM and a second regional EGM;
calculating at least one ratio out of:
an average ratio of the average duration of the first regional base line and the second regional base line to the reference cycle of the arrhythmia; and
for each base line, a ratio of the duration of the base line to the reference cycle of the arrhythmia; and
classifying the corresponding region of the heart according to its degree of involvement in perpetuation of the AF, the degree of involvement of the region being a function of the ratio or ratios calculated;
the other steps of the method being carried out by replacing:
local recording by regional recording and
area by region.

9. A method for identifying target areas of a heart of a patient likely to be involved in a perpetuation of atrial fibrillation according to claim 1, comprising an apparatus for identifying areas of the heart likely to be involved in the perpetuation of atrial fibrillation, comprising a digital analyzer and a digital mapper,
wherein the digital analyzer implements the method as claimed in claim 1;
the digital mapper being capable of generating a map of the heart of the patient on which the classification of the areas of the heart is formed.

10. A computer program comprising a series of instructions which implement the steps of: obtaining a reference cycle, determining an average duration of a first base line and a second base line between a first local EGM and a second local EGM, calculating at least one of the ratios, and classifying the corresponding area according to the method of claim 1, executed by a processor.

11. A non-transient and computer-readable storage medium comprising a computer program as claimed in claim 10.

12. A method for identifying target regions of a heart of a patient likely to be involved in a perpetuation of atrial fibrillation (AF), comprising:
taking a plurality of regional recordings of the heart of the patient during a measurement window, each regional recording corresponding to a region of the heart of the patient combining a plurality of areas, the method further comprising:
obtaining a reference cycle of an arrhythmia, the reference cycle being an average duration of a first base line and a second base line between a first depolarization and a second depolarization of a local recording corresponding to a healthy area of the heart of the patient; and
for each regional recording:
determining an average duration of a first base line and a second base line between the first depolarization and the second depolarizations of the regional recordings;
calculating at least one ratio out of:
an average ratio of the average duration of the first base line and the second base line to the reference cycle of the arrhythmia;
for each base line, a ratio of the duration of the base line to the reference cycle of the arrhythmia;
classifying the corresponding region of the heart according to its degree of involvement in the perpetuation of the AF, the degree of involvement of the region being a function of the ratio or ratios calculated; and
generating and displaying a map of the heart of the patient on which the classified areas of the heart are formed.

13. The method as claimed in claim 12, in which a region is classified as a non-target region if the average ratio or if all the ratios calculated is/are greater than or equal to a first value,
the region being otherwise classified as a true or false positive target region.

14. The method as claimed in claim 13, in which a region is classified as a true or false positive priority target region if the average ratio or at least one ratio calculated is less than or equal to a second value.

15. The method as claimed in claim 14, in which a region is classified as a true or false positive secondary target region if the average ratio or at least one ratio calculated lies between the second value and a third value lying between the first and second values; and the region is classified as a true or false positive tertiary target region if the average ratio or at least one ratio calculated lies between the third value and the first value.

16. The method as claimed in claim 12, in which the classification of each of the regions of the heart is also a function of a repetition in the corresponding regional recording of the base lines with calculated ratio of repetitive values;

a target region being a true positive if the repetition is proven.

17. The method as claimed in claim 12, in which the classification of each of the regions of the heart is also a function of an average of amplitude values of depolarizations of the corresponding regional recording;

a target region being a true positive if the average of the amplitude values is less than a given threshold value.

18. The method as claimed in claim 12, in which the classification of each of the regions of the heart is also a function of a repetition in the corresponding regional recording of the base lines with calculated ratio of repetitive values and a function of an average of amplitude values of depolarizations of the corresponding regional recordings;

a target region being a true positive if the repetition is proven and if the average of the amplitude values is greater than a given threshold value.

\* \* \* \* \*